(12) United States Patent
Giannetti et al.

(10) Patent No.: US 9,168,105 B2
(45) Date of Patent: Oct. 27, 2015

(54) DEVICE FOR SURGICAL INTERVENTIONS

(75) Inventors: Arnaldo Giannetti, Crescentino (IT); Laura Ghione, Turin (IT); Paolo Gaschino, Castagneto Po-Torino (IT); Giovanni Righini, Chivasso (IT)

(73) Assignee: Sorin Group Italia S.r.l., Milan (IT)

( * ) Notice: Subject to any disclaimer, the term of this patent is extended or adjusted under 35 U.S.C. 154(b) by 380 days.

(21) Appl. No.: 12/465,269

(22) Filed: May 13, 2009

(65) Prior Publication Data
US 2010/0292783 A1 Nov. 18, 2010

(51) Int. Cl.
*A61B 19/00* (2006.01)
*A61B 1/06* (2006.01)
*A61F 2/24* (2006.01)

(52) U.S. Cl.
CPC ........... *A61B 19/5202* (2013.01); *A61B 1/0676* (2013.01); *A61B 1/0684* (2013.01); *A61F 2/2436* (2013.01); *A61B 2019/521* (2013.01); *A61B 2019/5206* (2013.01); *A61F 2/2412* (2013.01)

(58) Field of Classification Search
CPC .... A61B 1/0676; A61B 1/07; A61B 19/5202; A61B 19/5212; A61B 2019/5206; A61B 2019/521; A61B 2019/5217; A61F 2/24; A61F 2/2409; A61F 2/2412; A61F 2/2427; A61F 2/243; A61F 2/2466; A61F 2/2696; A61F 2002/2484
USPC ............... 623/2.11, 2.38, 1.11, 902, 904, 2.1, 623/2.12, 2.17, 2.36, 23.68, 1.12; 606/108, 606/194, 192, 13–16; 600/107, 178–182, 600/200
See application file for complete search history.

(56) References Cited

U.S. PATENT DOCUMENTS

| | | | |
|---|---|---|---|
| 3,514,131 A | 5/1970 | McKinney |
| 3,671,979 A | 6/1972 | Moulopoulos |
| 4,011,947 A | 3/1977 | Sawyer |
| 4,056,854 A | 11/1977 | Boretos et al. |
| 4,220,151 A | 9/1980 | Whitney |
| 4,477,930 A | 10/1984 | Totten et al. |
| 4,601,706 A | 7/1986 | Aillon |
| 4,624,822 A | 11/1986 | Arru et al. |
| 4,684,364 A | 8/1987 | Sawyer et al. |

(Continued)

FOREIGN PATENT DOCUMENTS

| | | |
|---|---|---|
| DE | 29919625 U1 | 2/2000 |
| DE | 19546692 C2 | 11/2002 |

(Continued)

OTHER PUBLICATIONS

European Search Report Issued in EP 09160184 dated Oct. 22, 2009.

(Continued)

*Primary Examiner* — Jocelin Tanner
(74) *Attorney, Agent, or Firm* — Faegre Baker Daniels LLP

(57) ABSTRACT

A device for locating an operational unit within a patient's body within the framework of a minimally-invasive surgery intervention includes a shaft having a distal end carrying an operational unit. The device includes an illuminator located at the distal end of the shaft. The illuminator is selectively adjustable to provide a selectively variable lighting field in correspondence with the operational unit. The device may be, for example, a delivery system for a heart valve or a balloon device for post-dilation of such a heart valve once implanted.

18 Claims, 2 Drawing Sheets

(56) References Cited

U.S. PATENT DOCUMENTS

| | | | |
|---|---|---|---|
| 4,722,725 A | 2/1988 | Sawyer et al. | |
| 4,732,152 A | 3/1988 | Wallsten et al. | |
| 4,758,151 A | 7/1988 | Arru et al. | |
| 4,777,951 A | 10/1988 | Cribier et al. | |
| 4,784,644 A | 11/1988 | Sawyer et al. | |
| 4,994,077 A | 2/1991 | Dobben | |
| 5,057,092 A | 10/1991 | Webster, Jr. | |
| 5,084,151 A | 1/1992 | Vallana et al. | |
| 5,123,919 A | 6/1992 | Sauter et al. | |
| 5,133,845 A | 7/1992 | Vallana et al. | |
| 5,181,911 A | 1/1993 | Shturman | |
| 5,201,757 A | 4/1993 | Heyn et al. | |
| 5,287,848 A * | 2/1994 | Cubb et al. | 128/200.26 |
| 5,304,189 A | 4/1994 | Goldberg et al. | |
| 5,312,393 A * | 5/1994 | Mastel | 606/4 |
| 5,332,402 A | 7/1994 | Teitelbaum | |
| 5,370,684 A | 12/1994 | Vallana et al. | |
| 5,370,685 A | 12/1994 | Stevens | |
| 5,387,247 A | 2/1995 | Vallana et al. | |
| 5,397,351 A | 3/1995 | Pavcnik et al. | |
| 5,411,552 A | 5/1995 | Andersen et al. | |
| 5,423,886 A | 6/1995 | Arru et al. | |
| 5,433,723 A | 7/1995 | Lindenberg et al. | |
| 5,445,608 A * | 8/1995 | Chen et al. | 604/20 |
| 5,445,646 A | 8/1995 | Euteneuer et al. | |
| 5,545,214 A | 8/1996 | Stevens | |
| 5,554,185 A | 9/1996 | Block et al. | |
| 5,556,414 A | 9/1996 | Turi | |
| 5,662,712 A * | 9/1997 | Pathak et al. | 623/23.64 |
| 5,693,083 A | 12/1997 | Baker et al. | |
| 5,766,151 A | 6/1998 | Valley et al. | |
| 5,772,693 A | 6/1998 | Brownlee | |
| 5,824,064 A | 10/1998 | Taheri | |
| 5,840,081 A | 11/1998 | Andersen et al. | |
| 5,849,005 A | 12/1998 | Garrison et al. | |
| 5,855,597 A | 1/1999 | Jayaraman | |
| 5,855,601 A | 1/1999 | Bessler et al. | |
| 5,871,489 A * | 2/1999 | Ovil | 606/148 |
| 5,925,063 A | 7/1999 | Khosravi | |
| 5,951,600 A | 9/1999 | Lemelson | |
| 5,954,766 A | 9/1999 | Zadno-Azizi et al. | |
| 5,957,949 A | 9/1999 | Leonhardt et al. | |
| 5,968,068 A | 10/1999 | Dehdashtian et al. | |
| 5,980,570 A | 11/1999 | Simpson | |
| 6,010,530 A | 1/2000 | Goicoechea | |
| 6,010,531 A | 1/2000 | Donlon et al. | |
| 6,019,756 A * | 2/2000 | Mueller et al. | 606/7 |
| 6,019,790 A * | 2/2000 | Holmberg et al. | 623/2.11 |
| 6,029,671 A | 2/2000 | Stevens et al. | |
| 6,030,360 A | 2/2000 | Biggs | |
| 6,106,497 A | 8/2000 | Wang | |
| 6,125,852 A | 10/2000 | Stevens et al. | |
| 6,139,572 A | 10/2000 | Campbell et al. | |
| 6,168,614 B1 | 1/2001 | Andersen et al. | |
| 6,174,307 B1 * | 1/2001 | Daniel et al. | 606/15 |
| 6,251,093 B1 | 6/2001 | Valley et al. | |
| 6,299,638 B1 | 10/2001 | Sauter | |
| 6,309,382 B1 | 10/2001 | Garrison et al. | |
| 6,346,071 B1 | 2/2002 | Mussivand | |
| 6,395,017 B1 | 5/2002 | Dwyer et al. | |
| 6,402,780 B2 | 6/2002 | Williamson, IV et al. | |
| 6,416,474 B1 | 7/2002 | Penner et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,482,228 B1 | 11/2002 | Norred | |
| 6,572,642 B2 | 6/2003 | Rinaldi et al. | |
| 6,582,462 B1 | 6/2003 | Andersen et al. | |
| 6,607,553 B1 * | 8/2003 | Healy et al. | 623/1.11 |
| 6,641,558 B1 | 11/2003 | Aboul-Hosn et al. | |
| 6,645,197 B2 | 11/2003 | Garrison et al. | |
| 6,645,220 B1 | 11/2003 | Huter et al. | |
| 6,652,578 B2 | 11/2003 | Bailey et al. | |
| 6,685,739 B2 | 2/2004 | DiMatteo et al. | |
| 6,726,648 B2 | 4/2004 | Kaplon et al. | |
| 6,726,651 B1 | 4/2004 | Robinson et al. | |
| 6,726,712 B1 | 4/2004 | Raeder-Devens et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,434 B2 | 8/2004 | Liddicoat et al. | |
| 6,805,711 B2 | 10/2004 | Quijano et al. | |
| 6,830,584 B1 | 12/2004 | Seguin | |
| 6,830,585 B1 | 12/2004 | Artof et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,913,618 B2 | 7/2005 | Denardo et al. | |
| 6,945,957 B2 | 9/2005 | Freyman | |
| 6,964,673 B2 | 11/2005 | Tsugita et al. | |
| 6,974,464 B2 | 12/2005 | Quijano et al. | |
| 6,981,942 B2 | 1/2006 | Khaw et al. | |
| 6,991,646 B2 | 1/2006 | Clerc et al. | |
| 7,001,423 B2 | 2/2006 | Euteneuer et al. | |
| 7,018,406 B2 | 3/2006 | Seguin et al. | |
| 7,018,408 B2 | 3/2006 | Bailey et al. | |
| 7,041,132 B2 | 5/2006 | Quijano et al. | |
| 7,044,966 B2 | 5/2006 | Svanidze et al. | |
| 7,077,801 B2 | 7/2006 | Haverich | |
| 7,101,396 B2 | 9/2006 | Artof et al. | |
| 7,144,364 B2 | 12/2006 | Barbut et al. | |
| 7,156,872 B2 | 1/2007 | Strecker | |
| 7,195,641 B2 | 3/2007 | Palmaz et al. | |
| 7,201,761 B2 | 4/2007 | Woolfson et al. | |
| 7,329,279 B2 | 2/2008 | Haug et al. | |
| 7,338,467 B2 | 3/2008 | Lutter | |
| 7,338,520 B2 | 3/2008 | Bailey et al. | |
| 7,374,571 B2 | 5/2008 | Pease et al. | |
| RE40,377 E | 6/2008 | Williamson, IV et al. | |
| 7,399,315 B2 | 7/2008 | Iobbi | |
| 7,544,206 B2 | 6/2009 | Cohn | |
| 7,556,646 B2 | 7/2009 | Yang et al. | |
| 7,591,843 B1 | 9/2009 | Escano et al. | |
| 7,618,432 B2 | 11/2009 | Pedersen et al. | |
| 7,635,386 B1 | 12/2009 | Gammie | |
| 7,708,775 B2 | 5/2010 | Rowe et al. | |
| 7,896,915 B2 | 3/2011 | Guyenot et al. | |
| 8,475,521 B2 | 7/2013 | Suri et al. | |
| 8,486,137 B2 | 7/2013 | Suri et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0039450 A1 | 11/2001 | Pavcnik et al. | |
| 2001/0044591 A1 | 11/2001 | Stevens et al. | |
| 2002/0029075 A1 | 3/2002 | Leonhardt | |
| 2002/0042651 A1 | 4/2002 | Liddicoat et al. | |
| 2002/0045846 A1 | 4/2002 | Kaplon et al. | |
| 2002/0045929 A1 | 4/2002 | Diaz | |
| 2002/0058995 A1 | 5/2002 | Stevens | |
| 2002/0099431 A1 | 7/2002 | Armstrong et al. | |
| 2002/0107531 A1 | 8/2002 | Schreck et al. | |
| 2002/0117264 A1 | 8/2002 | Rinaldi et al. | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0033000 A1 | 2/2003 | DiCaprio et al. | |
| 2003/0036795 A1 | 2/2003 | Andersen et al. | |
| 2003/0055495 A1 | 3/2003 | Pease et al. | |
| 2003/0109924 A1 | 6/2003 | Cribier | |
| 2003/0130729 A1 | 7/2003 | Paniagua et al. | |
| 2003/0153974 A1 | 8/2003 | Spenser et al. | |
| 2003/0163194 A1 | 8/2003 | Quijano et al. | |
| 2003/0191521 A1 | 10/2003 | Denardo et al. | |
| 2003/0191528 A1 | 10/2003 | Quijano et al. | |
| 2004/0034411 A1 | 2/2004 | Quijano et al. | |
| 2004/0039371 A1 | 2/2004 | Tockman et al. | |
| 2004/0039436 A1 | 2/2004 | Spenser et al. | |
| 2004/0039442 A1 | 2/2004 | St. Goar et al. | |
| 2004/0049266 A1 | 3/2004 | Anduiza et al. | |
| 2004/0055606 A1 | 3/2004 | Hendricksen et al. | |

(56) References Cited

U.S. PATENT DOCUMENTS

| | | |
|---|---|---|
| 2004/0078072 A1 | 4/2004 | Tu et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0127848 A1 | 7/2004 | Freyman |
| 2004/0147993 A1 | 7/2004 | Westlund et al. |
| 2004/0186563 A1 | 9/2004 | Lobbi |
| 2004/0215333 A1 | 10/2004 | Duran et al. |
| 2004/0236170 A1 | 11/2004 | Kim |
| 2004/0249413 A1 | 12/2004 | Allen et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2005/0278010 A1* | 12/2005 | Richardson .................. 623/1.11 |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Levin et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0005131 A1 | 1/2007 | Taylor |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1 | 7/2007 | George et al. |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1* | 8/2008 | Cerier .......................... 606/139 |
| 2008/0262507 A1 | 10/2008 | Righini et al. |
| 2009/0069886 A1 | 3/2009 | Steinberg et al. |
| 2009/0069887 A1 | 3/2009 | Righini |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti |
| 2010/0292784 A1 | 11/2010 | Giannetti |
| 2012/0053684 A1 | 3/2012 | Righini et al. |
| 2013/0123915 A1 | 5/2013 | Giannetti et al. |

FOREIGN PATENT DOCUMENTS

| | | |
|---|---|---|
| DE | 19857887 B4 | 5/2005 |
| EP | 133420 B1 | 2/1988 |
| EP | 0155245 B1 | 5/1990 |
| EP | 0637454 B1 | 2/1995 |
| EP | 0592410 B1 | 10/1995 |
| EP | 0512359 B1 | 12/1996 |
| EP | 0515324 B1 | 12/1996 |
| EP | 0850607 A1 | 7/1998 |
| EP | 0941716 B1 | 9/1999 |
| EP | 1057460 A1 | 12/2000 |
| EP | 1059271 A1 | 12/2000 |
| EP | 1356763 A2 | 10/2003 |
| EP | 1356793 A2 | 10/2003 |
| EP | 0852481 B1 | 2/2004 |
| EP | 1440671 A2 | 7/2004 |
| EP | 1088529 B1 | 6/2005 |
| EP | 955895 B1 | 8/2005 |

(56) References Cited

FOREIGN PATENT DOCUMENTS

| | | |
|---|---|---|
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1978895 B1 | 10/2008 |
| EP | 1986579 B1 | 11/2008 |
| EP | 1570809 B1 | 1/2009 |
| EP | 2033581 A1 | 3/2009 |
| EP | 2033597 A1 | 3/2009 |
| FR | 2828091 A1 | 2/2003 |
| WO | WO9511055 A1 | 4/1995 |
| WO | WO 97/24989 A1 | 7/1997 |
| WO | WO 98/17202 A1 | 4/1998 |
| WO | WO 98/29057 A1 | 7/1998 |
| WO | WO9853761 A1 | 12/1998 |
| WO | WO 99/04728 A1 | 2/1999 |
| WO | WO9912483 A1 | 3/1999 |
| WO | WO 99/56665 A1 | 11/1999 |
| WO | WO 00/18303 A1 | 4/2000 |
| WO | WO 00/41525 A2 | 7/2000 |
| WO | WO 00/41652 A1 | 7/2000 |
| WO | WO 01/21244 A1 | 3/2001 |
| WO | WO 01/62189 A1 | 8/2001 |
| WO | WO 01/64137 A1 | 9/2001 |
| WO | WO 01/76510 A2 | 10/2001 |
| WO | WO 02/41789 A2 | 5/2002 |
| WO | WO 02/47575 A2 | 6/2002 |
| WO | WO 02/076348 A1 | 10/2002 |
| WO | WO03047468 A1 | 6/2003 |
| WO | WO 03/003943 A3 | 11/2003 |
| WO | WO 03/094797 A1 | 11/2003 |
| WO | WO2004019825 A1 | 3/2004 |
| WO | WO2004028399 A2 | 4/2004 |
| WO | WO 2004/089253 A1 | 10/2004 |
| WO | WO 2005/046525 A1 | 5/2005 |
| WO | WO 2005/065200 A2 | 7/2005 |
| WO | WO 2005/096993 A1 | 10/2005 |
| WO | WO 2005/104957 A2 | 11/2005 |
| WO | WO2006009690 A1 | 1/2006 |
| WO | WO2006014233 A2 | 2/2006 |
| WO | WO 2006/054107 A2 | 5/2006 |
| WO | WO 2006/063199 A2 | 6/2006 |
| WO | WO2006076890 A1 | 7/2006 |
| WO | WO 2006/086135 A2 | 8/2006 |
| WO | WO2006089517 A1 | 8/2006 |
| WO | WO 2006/116558 A2 | 11/2006 |
| WO | WO 2006/135551 A2 | 12/2006 |
| WO | WO 2006/138173 A2 | 12/2006 |
| WO | WO2007021708 A1 | 2/2007 |
| WO | WO2007033093 A2 | 3/2007 |
| WO | WO2007059252 A1 | 5/2007 |
| WO | WO 2007/071436 A2 | 6/2007 |
| WO | WO 2007/076463 A2 | 7/2007 |
| WO | WO2008031103 A2 | 3/2008 |
| WO | WO 2008/097589 A1 | 8/2008 |
| WO | WO 2008/125153 A1 | 10/2008 |
| WO | WO2008138584 A1 | 11/2008 |

OTHER PUBLICATIONS

European Search Report Issued in EP Application No. 09160183, dated Oct. 2, 2009, 6 pages.

European Search Report Issued in EP Application No. 09160186, dated Oct. 6, 2009, 5 pages.

European Search Report Issued in EP Application No. 07115951, dated Sep. 24, 2009, 8 pages.

Extended European Search Report issued in EP Application 06126552, dated Jun. 6, 2007, 7 pages.

Extended European Search Report issued in EP Application 06126556, dated Jul. 6, 2007, 13 pages.

Extended European Search Report Issued in EP Application 07115960, dated Jan. 24, 2008, 8 pages.

Extended European Search Report issued in EP Application 09158822, dated Sep. 9, 2009, 5 pages.

Ho, Paul C., "Percutaneous aortic valve replacement: A novel design of the delivery and deployment system", Minimally Invasive Therapy, 2008; 17:3; 190-194.

Huber, Christoph H. et al., "Direct-Access Valve Replacement: A Novel Approach for Off-Pump Valve Implantation Using Valved Stents", Journal of the American College of Cardiology, vol. 46, No. 2, 2005, pp. 366-370.

Partial European Search Report issued in EP App No. 06126556, mailed Apr. 16, 2007, 6 pages.

European Search Report issued in EP Application No. 08159301, mailed Dec. 30, 2008, 6 pages.

Partial European Search Report issued in EP Application No. 10155332, dated Jun. 9, 2011, 7 pages.

* cited by examiner

DEVICE FOR SURGICAL INTERVENTIONS

TECHNICAL FIELD

The present invention relates to devices for surgical interventions. More specifically, the invention relates to its possible application to minimally-invasive surgical techniques.

BACKGROUND

Expandable prosthetic valves typically include an expandable and collapsible anchoring structure or armature, which is able to support and fix the valve prosthesis in the implantation position, and prosthetic valve elements, generally in the form of leaflets or flaps, which are stably connected to the anchoring structure and are able to regulate blood flow.

These expandable prosthetic valves enable implantation using various minimally invasive or sutureless techniques. Exemplary applications for such an expandable valve prosthesis include aortic and pulmonary valve replacement. Various techniques are generally known for implanting an aortic valve prosthesis and include percutaneous implantation (e.g., transvascular delivery), dissection of the ascending aorta using minimally invasive thoracic access (e.g., mini-thoracotomy or mini-sternotomy), and transapical delivery wherein the aortic valve annulus is accessed through an opening near the apex of the left ventricle. The percutaneous and thoracic access approaches involve delivering the prosthesis in a direction opposing blood flow (i.e., retrograde), whereas the transapical approach involves delivering the prosthesis in the same direction as blood flow (i.e., antegrade).

SUMMARY

The present invention, according to one embodiment, is a device for implanting a prosthetic heart valve at an implantation site. The device includes a shaft having a distal end adapted to couple to the prosthetic heart valve and maintain the valve in a collapsed configuration, an illuminator selectively adjustable to provide a variable lighting field, the illuminator coupled at or near the distal end of the shaft, an optical fiber extending through at least a portion of the shaft, the optical fiber having a proximal end extending from a proximal end of the shaft and a distal end coupled to the illuminator, the optical fiber is adapted to transmit the lighting field from the illuminator to the distal end of the shaft, and an actuator coupled to the illuminator and adapted to effect a change to the variable lighting field.

The present invention, according to another embodiment, includes a device for locating an operational unit within a patient's body, the device including a shaft having a distal end carrying the operational unit, wherein the device includes an illuminator located at the distal end of the shaft, the illuminator selectively adjustable to provide a selectively variable lighting field at the operational unit.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
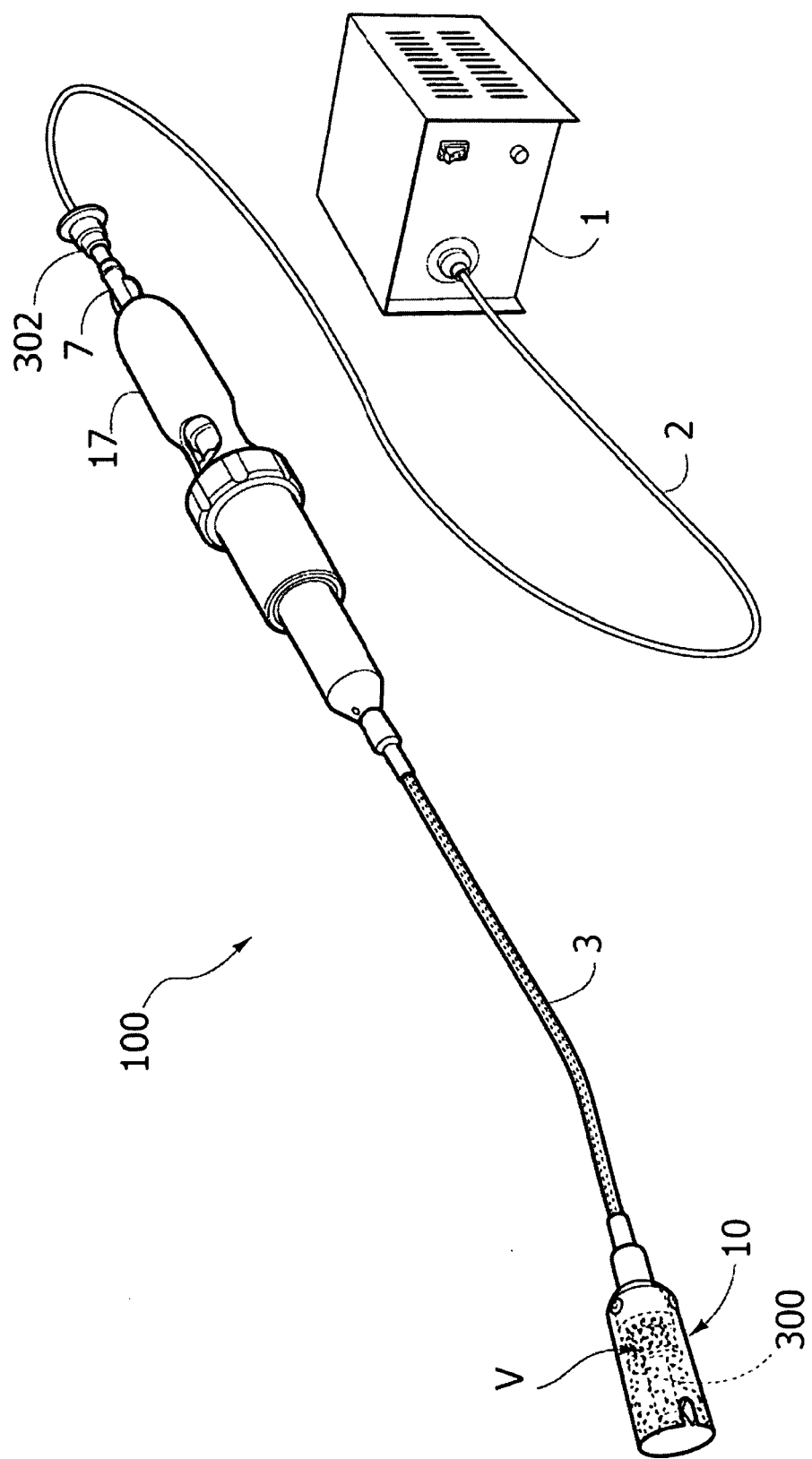
FIG. 1 is a general perspective of a first device as described herein.

FIG. 1 is a schematic view of a delivery system 100 for use in delivering a prosthetic heart valve V in a minimally-invasive surgical manner. According to various embodiments, the valve V is of the type disclosed in U.S. Publication 2006/0178740, which is incorporated herein by reference. According to various embodiments, the delivery system may be of the type disclosed in U.S. Publication 2008/0147182 and/or U.S. Publication 2008/0147180, which are both incorporated herein by reference. According to other embodiments, the delivery system may be of the type disclosed in co-pending, commonly assigned U.S. patent application Ser. No. 12/465,278, filed on even date herewith, entitled, "DEVICE FOR THE IN SITU DELIVERY OF HEART VALVES," commonly assigned U.S. patent application Ser. No. 12/465,262, filed on even date herewith, entitled, "DEVICE FOR THE IN SITU DELIVERY OF HEART VALVES," both of which are incorporated herein by reference.

As shown in FIG. 1, the device 100 includes a handle 17 for manipulation by a practitioner at the proximal end of the device 100 and a shaft 3 (which may be flexible or rigid) extending from the handle 17 to a holder portion 10 for the valve V. Once advanced to the location of the natural valve to be substituted, the prosthetic valve V is deployed by becoming disengaged from the holder portion 10 which previously kept the valve in a radially contracted condition. Once the valve is deployed and expanded at the desired implantation site, a common practice provides for post-dilation of the valve in order to consolidate the implantation conditions of the valve.

Figure 2:
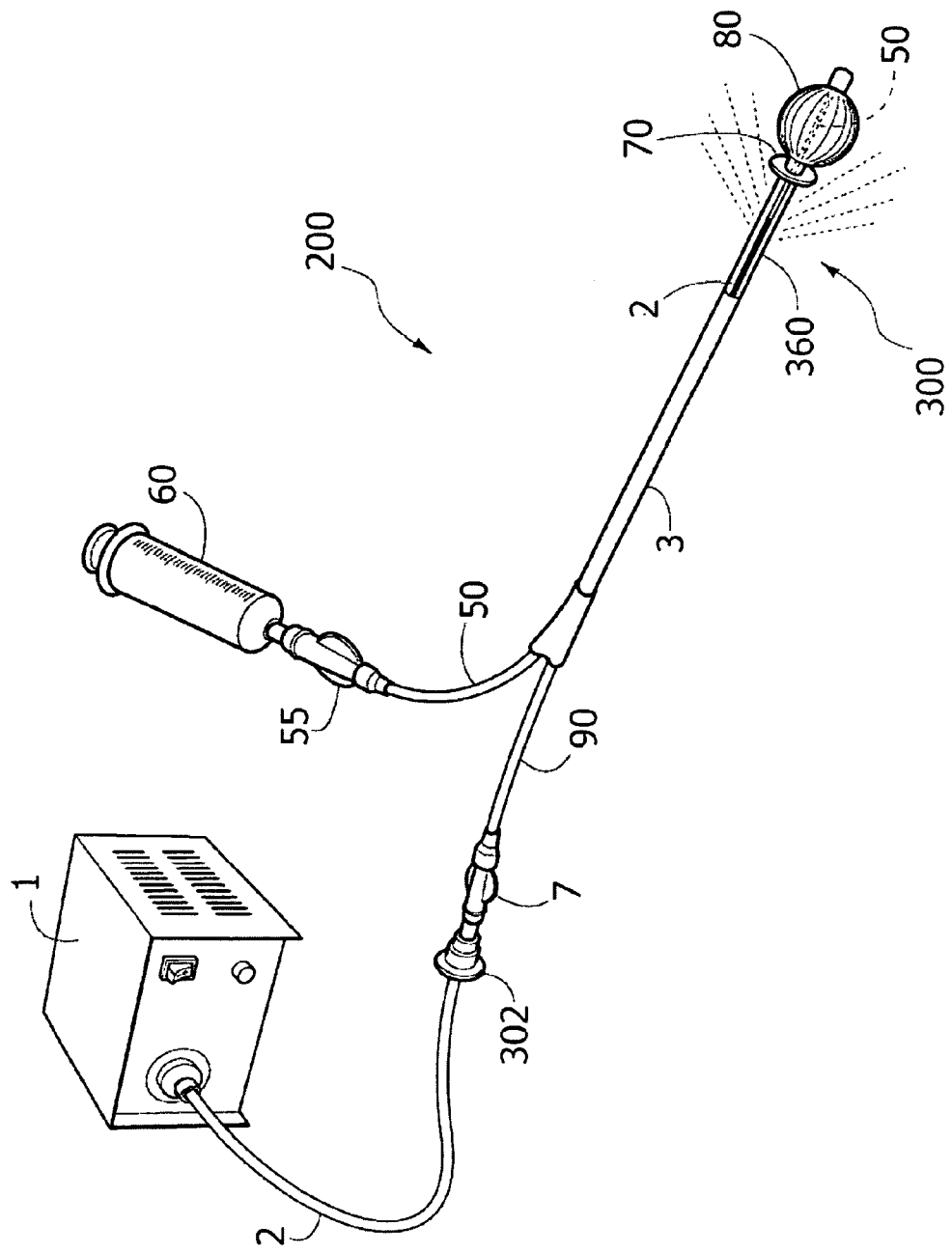
FIG. 2 is a general perspective of a second device as described herein.

FIG. 2 shows a device 200 to perform post-dilation of a valve such as the valve V considered in FIG. 1 after such a valve is arranged at an implantation side within a patient's body. The device 200 includes a flexible shaft 3 extending between a proximal end of the device including manipulation/actuation elements for the device 100 including, for example, an inflating syringe 60 connected via a connector 55 (luer-lock or the like) to an inflation conduit 50 to convey pressurized saline solution from the syringe 60 towards a balloon member 80 located at the distal end of the shaft 3. Reference 70 denotes a positioning ring located in proximity to the balloon 80 to facilitate exact positioning of the balloon 80 at the implantation site of the valve V to permit post-dilation.

The delivery system 100 and the post-dilation device 200 considered herein are exemplary of a class of devices for use in minimally-invasive interventions. These devices share a common general structure including an elongated shaft member carrying at its distal end an "operational" unit such as the valve holder 10 of FIG. 1 or the dilation balloon 80 of FIG. 2, the shaft member 3 enabling the practitioner to position the operational unit at the desired interventional site.

As indicated, further non-limiting examples of devices exhibiting such a basic structure are devices for the removal (ablation) of natural valve leaflets (e.g. in view of the implantation of a prosthetic heart valve) or sizer devices for use after removal of the natural valve leaflets to size the prosthetic valve implantation site.

The embodiments disclosed herein include a vision or lighting system to facilitate vision of the interventional site by the practitioner performing the intervention. An exemplary lighting system may include a light source 1 (of any known type (e.g., the device GLI 156P available from Fort Fibre Ottiche S.r.l. of Bergamo (Italy)).

An optical fiber member 2 (including either a single fiber or a bundle of fibers) connected to the source 1 extends into a connector 7 (e.g. luer lock or the like) located at the proximal end of the shaft and then into and along the shaft 3 to convey light produced by the source 1 through the device 100, 200 on to the operational unit (e.g. the valve holder 10 or the balloon 80). In one embodiment, the optical fiber member 2 extends in an axial duct 90 provided in the shaft 3 coaxial to the inflation conduit 50.

The optical fiber element 2 has a distal end located at the distal end element of the shaft 3 in correspondence with the operational unit 10, 80 to act as an illuminator 300, i.e. as a lighting source, to throw light in or into the area in the patient's body where the operational unit 10, 80 is located during the intervention e.g. to deliver the valve V at the implantation site or to post-dilate the valve V after positioning at the implantation site. The illuminator 300 permits the light radiation from the optical fiber element to provide lighting over a "lighting field" i.e. the area reached by the light radiation from the illuminator 300.

The practitioner can thus directly observe the region of the patient's body where the operational unit 10, 80 is located, while that region is covered, and thus illuminated, by the lighting field of the illuminator 300 even if the path of ambient light to the interventional site is restricted or obstructed (e.g. by the body structures of the patient).

In one embodiment, the illuminator 300 is simply comprised of the distal end of the fiber element 2. In one embodiment, the illuminator may include a reflector, diffuser or similar member. In one embodiment, the illuminator 300 is simply comprised of the distal end of the fiber element 2 put in a diffuser room. Fiber optics is an established technology to provide local illumination by providing a fixed lighting pattern of the portion of a body vessel which is being inspected via endoscopy.

In order to meet the requirements of non-invasive surgery, in an embodiment the illuminator 300 is made adjustable, so that the "lighting field" produced thereby is selectively variable. The area reached by the light radiation from the illuminator 300 can thus be modified by the practitioner, for example, depending on his/her varying needs for different interventions and/or during different steps in an intervention.

In one embodiment, making the illuminator adjustable to vary the area covered by the lighting action may involve varying (e.g. via actuator means such as micro actuators operated from the proximal end of the device 100, 200) the geometry and/or position of the reflector, diffuser or other optical member comprising the illuminator 300.

In one embodiment, making the illuminator adjustable to vary the area covered by the lighting action may simply involve making the element 2 adapted to be displaced axially with respect to the shaft 3, so that the point from which light is produced at the distal end of element 2 can be selectively advanced or retracted with respect to the operational unit 10, 80 depending on the specific needs of the practitioner.

In the exemplary embodiment illustrated, a fiber block unit 302 (e.g., of the type commercially available under the trade designation Tuohy Borst 80363 from Qosina of 150 Executive Drive, Edgewood, N.Y. (USA)) is mounted on the fiber element 2 in proximity to the connector 7 to selectively lock and unlock the fiber element 2. When unlocked, the element 2 becomes axially slidable with respect to the shaft 3 so that the position of the illuminator end 300 can be selectively varied by the practitioner. Once the desired position (i.e. illumination field) has been achieved, the unit 302 can be actuated to lock the element 2 in order to prevent any undesired displacement of the element 2 along the shaft.

While an optical fiber element has been described herein as exemplary of means for conveying light from the proximal end to the distal end of the device 100, 200, those of skill in the art will appreciate that other solutions can be used for the same purpose such as e.g. mirror arrangements or other types of conduit for conveying light.

In one embodiment, the illuminator 300 may be an autonomous light source such as a Light Emitting Diode (LED) module. LEDs (e.g. of the high-flux type) are becoming increasingly popular as lighting sources, for use e.g. in so-called luminaries for ambience lighting or heavy-duty applications such as street lighting. LED lighting sources exhibit a number of features such as small dimensions, high efficiency, low heat generation and low-voltage (i.e. non-hazardous) operation which make them good candidates for use in an arrangement as disclosed herein.

In embodiments wherein the illuminator 300 is an autonomous light source, conveying light radiation along the shaft 3 is no longer required and an electrical line (e.g. a wire pair) will be provided in the place of the element 2 to supply energizing power to the illuminator 300 from the proximal end of the device 100, 200.

In one embodiment, such a line may be made capable of being displaced axially with respect to the shaft 3, and thus act as an actuator permitting the illuminator 300 (e.g. a LED) to be selectively moved, i.e. advanced or retracted, with respect to the operational unit 10, 80.

In any of the embodiments considered herein, the shaft member 3 may include a distal transparent portion (see e.g. 360 in FIG. 2) for light radiation from the illuminator 300 (e.g. the distal end of the fiber element 2) to propagate therethrough if and/or when the illuminator 300 is located within the shaft 3.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A device for implanting a minimally-invasive prosthetic heart valve at an implantation site, the prosthetic heart valve including an anchoring structure and a plurality of leaflets, the prosthetic heart valve having a collapsed configuration for delivery and an expanded configuration for anchoring at the implantation site, the device including:

a shaft extending from a handle at a proximal end to a valve holder at a distal end, the valve holder adapted to couple to the prosthetic heart valve and maintain the prosthetic heart valve in the collapsed configuration, the shaft having a diameter at the proximal end where the shaft extends from the handle that is smaller than a diameter of the handle;

an illuminator selectively adjustable to provide a variable lighting field, the illuminator coupled at or near the distal end of the shaft;

an optical fiber extending through at least a portion of the shaft, the optical fiber having a proximal end extending from the proximal end of the shaft and a distal end coupled to the illuminator, the optical fiber is adapted to transmit the lighting field from the illuminator to the distal end of the shaft, and adapted to be axially slidable with respect to the shaft to selectively displace the illuminator to provide a selectively variable lighting field;

an actuator coupled to the illuminator and adapted to effect a change to the variable lighting field; and a lock means actuatable to permit the optical fiber to be axially slidable with respect to the shaft to allow the illuminator to be positioned at multiple selective locations in order to provide the selectively variable lighting field, and the lock means being actuatable to prevent the optical fiber from being axially slidable with respect to the shaft in order to lock the illuminator at a particular selective location, wherein the lock means is located proximal to the handle and proximal to the valve holder.

2. The device of claim 1, including adjustment means at a proximal end of the device whereby at least one of the geometry and the position of the illuminator to provide the selectively variable lighting field is made variable.

3. The device of claim 1, wherein the optical fiber conveys light radiation along the shaft, and the illuminator includes the distal end of the optical fiber.

4. The device of claim 1, wherein the shaft includes a distal transparent portion for light radiation from the illuminator to propagate therethrough.

5. The device of claim 1, wherein the actuator is a microactuator.

6. The device of claim 5, wherein the microactuator is operable from a proximal end of the device and wherein at least one of the geometry and the position of the illuminator are variable in order to provide the selectively variable lighting field.

7. A device for minimally-invasive implantation of a prosthetic heart valve within a patient's body, the prosthetic heart valve including an anchoring structure and a plurality of leaflets, the prosthetic heart valve having a collapsed configuration for delivery and an expanded configuration for anchoring at an implantation site, the device including a shaft extending from a handle at a proximal end to a valve holder at a distal end for maintaining the prosthetic heart valve in the collapsed configuration, the shaft having a diameter at the proximal end where the shaft extends from the handle that is smaller than a diameter of the handle, wherein the device includes an illuminator located at the distal end of the shaft, the illuminator selectively adjustable to provide a selectively variable lighting field at an operational unit, wherein the illuminator includes an autonomous light source located at the distal end of the shaft, the device further including an electrical line to convey along the shaft electrical power for energizing the autonomous light source, wherein the electrical line is adapted to be axially slidable with respect to the shaft to selectively displace the illuminator to provide the selectively variable lighting field at the operational unit; and a lock means actuatable to permit the electrical line to be axially slidable with respect to the shaft to allow the autonomous light source to be positioned at multiple selective locations in order to provide the selectively variable lighting field, and the lock means being actuatable to prevent the electrical line from being axially slidable with respect to the shaft in order to lock the illuminator at a particular selective location, wherein the lock means is located proximal to the handle and proximal to the valve holder.

8. The device of claim 7, wherein the operational unit is selected out of a heart valve delivery unit, a post-dilation balloon member for a heart valve, a unit for the ablation of natural valve leaflets, and a sizer unit for sizing a valve implantation site.

9. The device of claim 7, wherein the illuminator includes at least one of a reflector and a diffuser.

10. The device of claim 7, wherein the autonomous light source is a LED source.

11. The device of claim 7, wherein the shaft includes a distal transparent portion for light radiation from the illuminator to propagate therethrough.

12. A device for minimally-invasive implantation of a prosthetic heart valve within a patient's body, the prosthetic heart valve including an anchoring structure and a plurality of leaflets, the prosthetic heart valve having a collapsed configuration for delivery and an expanded configuration for anchoring at an implantation site, the device including a shaft extending from a handle at a proximal end to a valve holder at a distal end for maintaining the prosthetic heart valve in the collapsed configuration, the shaft having a diameter at the proximal end where the shaft extends from the handle that is smaller than a diameter of the handle, wherein the device includes an illuminator located at the distal end of the shaft, the illuminator selectively adjustable to provide a selectively variable lighting field at an operational unit, and an actuator coupled to the illuminator that is adapted to effect a change to the variable lighting field, wherein the illuminator includes an autonomous light source located at the distal end of the shaft, the device further including an electrical line to convey along the shaft electrical power for energizing the autonomous light source, wherein the electrical line is adapted to be axially slidable with respect to the shaft to selectively displace the illuminator to provide the selectively variable lighting field at the operational unit; and a lock means actuatable to permit the electrical line to be axially slidable with respect to the shaft to allow the autonomous light source to be positioned at multiple selective locations in order or provide the selectively variable lighting field, and the lock means being actuatable to prevent the electrical line from being axially slidable with respect to the shaft in order to lock the illuminator at a particular selective location, wherein the lock means is located proximal to the handle and proximal to the valve holder.

13. The device of claim 12, wherein the actuator is a microactuator.

14. The device of claim 13, wherein the microactuator is operable from a proximal end of the device and wherein at least one of the geometry and the position of the illuminator are variable in order to provide the selectively variable lighting field.

15. The device of claim 12, wherein the shaft includes a distal transparent portion for light radiation from the illuminator to propagate therethrough.

16. The device of claim 12, wherein the operational unit is selected out of a heart valve delivery unit, a post-dilation balloon member for a heart valve, a unit for the ablation of natural valve leaflets, and a sizer unit for sizing a valve implantation site.

17. The device of claim 12, wherein the illuminator includes at least one of a reflector and a diffuser.

18. The device of claim 12, wherein the autonomous light source is a LED source.

* * * * *